(12) United States Patent
Hunt

(10) Patent No.: US 7,627,369 B2
(45) Date of Patent: Dec. 1, 2009

(54) QT-INTERVAL MEASUREMENT IN THE ELECTROCARDIOGRAM

(75) Inventor: Anthony Charles Hunt, Yelverton (GB)

(73) Assignee: PSI Heartsignals (Global) Limited, Glasgow (GB)

( * ) Notice: Subject to any disclaimer, the term of this patent is extended or adjusted under 35 U.S.C. 154(b) by 148 days.

(21) Appl. No.: 10/575,340

(22) PCT Filed: Oct. 10, 2003

(86) PCT No.: PCT/GB03/04436

§ 371 (c)(1),
(2), (4) Date: Jun. 21, 2007

(87) PCT Pub. No.: WO2005/044102

PCT Pub. Date: May 19, 2005

(65) Prior Publication Data

US 2008/0262366 A1    Oct. 23, 2008

(51) Int. Cl.
*A61B 5/0452* (2006.01)

(52) U.S. Cl. ....................... 600/516; 600/509

(58) Field of Classification Search ................. 600/512, 600/515–518; 607/25
See application file for complete search history.

(56) References Cited

U.S. PATENT DOCUMENTS

| | | | | |
|---|---|---|---|---|
| 5,419,338 | A | 5/1995 | Sarma et al. | 600/516 |
| 5,560,368 | A | 10/1996 | Berger | 600/517 |
| 5,560,370 | A | 10/1996 | Verrier et al. | 600/518 |
| 5,792,065 | A * | 8/1998 | Xue et al. | 600/516 |
| 6,370,423 | B1 * | 4/2002 | Guerrero et al. | 600/513 |
| 6,615,075 | B2 * | 9/2003 | Mlynash et al. | 600/513 |
| 2002/0095095 | A1 | 7/2002 | Callahan et al. | 600/516 |
| 2002/0138013 | A1 * | 9/2002 | Guerrero et al. | 600/509 |

(Continued)

FOREIGN PATENT DOCUMENTS

WO    WO00/62668    10/2000

(Continued)

OTHER PUBLICATIONS

Savelieva I. et al. "Agreement and reproducibility of automatic versus manual measurement of QT dispersion", American Journal of Cardiology, Cahners Publishing Co., Newton, MA, vol. 81, 1998, pp. 471-477, SP002955972 ISSN: 0002-9149.

(Continued)

*Primary Examiner*—Carl H Layno
*Assistant Examiner*—Gary A Porter, Jr.
(74) *Attorney, Agent, or Firm*—Heslin Rothenberg Farley & Mesiti P.C.

(57) ABSTRACT

A method and apparatus for measuring the QT interval of an electrocardiogram (ECG) signal is provided wherein the end of the T wave is identified from ECG data. The end of the T wave is defined as the first time of intersection at which an upright T wave of a first set of derived ECG signal data intersects an inverted T wave of a second set of derived ECG signal data. The intersection of the two sets of ECG data is along an isoelectric line within the trough after the positive T wave peak when the superimposed isoelectric baselines from the upright and inverted ECG signals demonstrate the best least squares fit.

39 Claims, 5 Drawing Sheets

U.S. PATENT DOCUMENTS

2003/0100926 A1     5/2003    Dam ........................... 607/25
2004/0059203 A1*   3/2004    Guerrero et al. ............ 600/300

FOREIGN PATENT DOCUMENTS

WO      WO02/00113     1/2002

OTHER PUBLICATIONS

Cohen T.J. et al. "A simple electrocardiographic algorithm for detecting ventricular tachycardia", PACE—Pacing and Clinical Electrophysiology, Futura Publishing Company, Inc., vol. 20, No. 10, Part 1, Oct. 1, 1997, pp. 2412-2418, XP000722422 ISSN: 0147-8389.

* cited by examiner

QT-INTERVAL MEASUREMENT IN THE ELECTROCARDIOGRAM

CROSS-REFERENCE TO RELATED APPLICATIONS

This application is a Section 371 filing of International Application No. PCT/GB2003/004436 filed Oct. 10, 2003 and published in English as WO 2005/044102 A1 on May 19, 2005, which application is incorporated herein by reference, in its entirety.

BACKGROUND OF THE INVENTION

The present invention relates to methods and apparatus for measuring the QT interval on an electrocardiogram.

An electrocardiogram (ECG) measures the instantaneous voltage potential difference of myocardial electrical activity in a number of lead vectors. "Leads" (or signals) are obtained from a subject using electrodes placed on their skin, placed on standardised locations around the body. Each electrode is connected to a signal processing apparatus via a respective wire (or "lead"). The term "lead" commonly refers to either a physical wire to an electrode or to an ECG signal itself. Commonly 12 different leads are used although it is also known to collapse all the information to within three orthogonal X, Y and Z leads or three quasi-orthogonal leads consisting of known ECG leads I, aVf and V2.

The durations of certain types of waves within the ECG give very important information. One important interval is the QT interval which is approximately 400 ms in duration. Variation in the QT interval is a known indicator of cardiac dysfunction. For example, an average increase in the QT interval of as little as 5-10 ms during pharmaceutical compound safety testing indicates the potential for the drug to induce a fatal cardiac rhythm disturbance if the compound were to be more widely prescribed. Therefore accurate measurement of the QT interval in the standard 12 lead ECG is of paramount importance when assessing the safety of a new drug.

Although the onset of the QT interval can be accurately measured by existing methods, there are difficulties measuring the accurate timing of the end of the "T wave" of the ECG due to the low frequency nature of the waveform, superaddition of an ECG "U wave", baseline drift of the signal and other superadded high frequency noise.

Automated methods to measure the QT interval with good reproducibility in a given ECG vector lead exist. However, they are not considered any more accurate than expert manual measurements hence they can give reproducibly wrong measurements. Even if the current automated methods to measure the QT interval were accurate, errors in measuring the real longest QT interval for the median signal of a 12 lead ECG vector arise because, in addition to the three quasi-orthogonal leads I, aVf and V2 which contain the longest QT interval information, there are nine further lead vectors containing noise and U waves which would contaminate the information from the orthogonal leads, causing measurement error.

BRIEF SUMMARY OF THE INVENTION

The present invention seeks to provide improved methods and apparatus for the measurement of the QT interval.

According to an aspect of the present invention, there is provided a method of measuring the QT interval of an electrocardiogram (ECG) signal wherein the end of the T wave is identified from ECG data, the end of the T wave being determined by reference to the timing of at least one intersection at which an upright T wave of a first set of derived ECG signal data intersects an inverted T wave of a second set of derived ECG signal data, the two sets of ECG data being superimposed so as to maximise their fit over a segment after the positive T wave peak.

The intersections can be detected visually on superimposed graphs. Preferably, however, they are detected automatically by numerical techniques. With this in mind, the skilled reader will appreciate that reference to "intersection" and "superimposition" should not be interpreted literally, provided that mathematically equivalent operations are applied.

The fit of said data may be maximised by a least squares calculation.

In one embodiment, the method comprises the steps of:
(a) acquiring ECG signal data,
(b) deriving a first set of reduced noise ECG signal data from the acquired ECG signal data,
(c) inverting the first reduced noise set of ECG signal data to derive an inverted set of reduced noise ECG signal data;
(d) identifying a portion of each set of ECG signal data corresponding to a segment after the T wave,
(e) calculating an offset such as to fit the first set of data to the inverted set of data over said segment;
(f) detecting at least one intersection between the first and inverted set of data by reference to said offset; and
(g) determining the end of said QT intervals by reference to the timing of the detected intersection(s).

The ECG signal data may acquired from, for example ECG electrodes and/or associated apparatus. Alternatively the ECG data may be acquired from a wide variety of storage or communications media, for example a computer memory or over a communications network.

In step (g) the end of the QT interval must be determined by the first point intersection. The end of the T wave is defined in one embodiment at the first point of intersection in said segment, provided there is at least one other point of intersection after a predetermined interval. Said interval can be varied according to the noise content in the segment of the ECG deemed to be the isoelectric line The step (b) may comprise calculating the median signal for each time from an ensemble of ECG signals for each lead to reduce low frequency baseline noise.

The method (b) may further comprise smoothing the median ensembled ECG signal with moving median filter to reduce high frequency noise.

The method (b) may also further comprise filtering the median smoothed, median ensembled ECG using a wavelet frequency thresholding technique which subtracts the magnitudes of any non-zero frequency components (noise) within the isoelectric baseline segment from the rest of the ECG thus further de-noising it.

The step (b) may further include vertically shifting the smoothed median ensembled ECG signal so that the minimum value after peak of T is zero.

The step (b) may further comprise the steps of detecting and correcting baseline drift in the first set of ECG data. The detecting step may for example include the testing for the presence of a single crossing of one isoelectric line (for example zero). The ensembled ECG can be rotated about a zero point or otherwise transformed to reconfigure the set of ECG data to have multiple crossings of said line (for example multiple zero minima).

The step (b) may further include applying a non-linear function such as squaring the amplitudes of the signal for all time instants, in order to accentuate features of interest and ensure positive deflections of the T wave.

The step (b) may further include summing the squared amplitudes of ensembled orthogonal leads over all time instants to give a squared resultant vector ensembled ECG.

The method may further include finding the beginning of the QT interval by an established method, for example from the median of ensembled ECG signals from all 12 leads.

The method may include calculating the QT interval by subtracting the beginning of QT from the calculated end of the T wave.

In one embodiment of the invention QT interval is measured for the squared vector resultant data derived from quasi-orthogonal or actual orthogonal XYZ leads, and the longest of QT measurements made in 3 dimensions is made. This has the benefit of avoiding any apparent change in the QT interval of a fixed direction vector which may be caused by a dynamic physiological change in direction of the resultant vector in three dimensions but without causing any change in length of the resultant vector QT interval.

The ECG signal data may be acquired in step (a) from the set of standard ECG leads including I, aVf and V2.

In another aspect of the invention, there is provided a record carrier wherein there are recorded program instructions for causing a programmable processor to perform the steps of the method as set forth above, or to implement an apparatus having the features set forth.

The present invention, further provides an apparatus for measuring the QT interval of an electrocardiogram (ECG) signal wherein there is provided means for identifying the end of then T wave from ECG data, the end of the T wave defined as the first time of intersection at which an upright T wave of a first set of derived ECG signal data intersects an inverted T wave of a second set of derived ECG signal data, the two sets of data being superimposed so as to maximise their fit over a segment after the positive T wave peak.

BRIEF DESCRIPTION OF THE DRAWINGS

Embodiments of the invention will now be described, by way of example only, by reference to the accompanying drawings, in which.

DETAILED DESCRIPTION OF THE EMBODIMENTS

Figure 1:
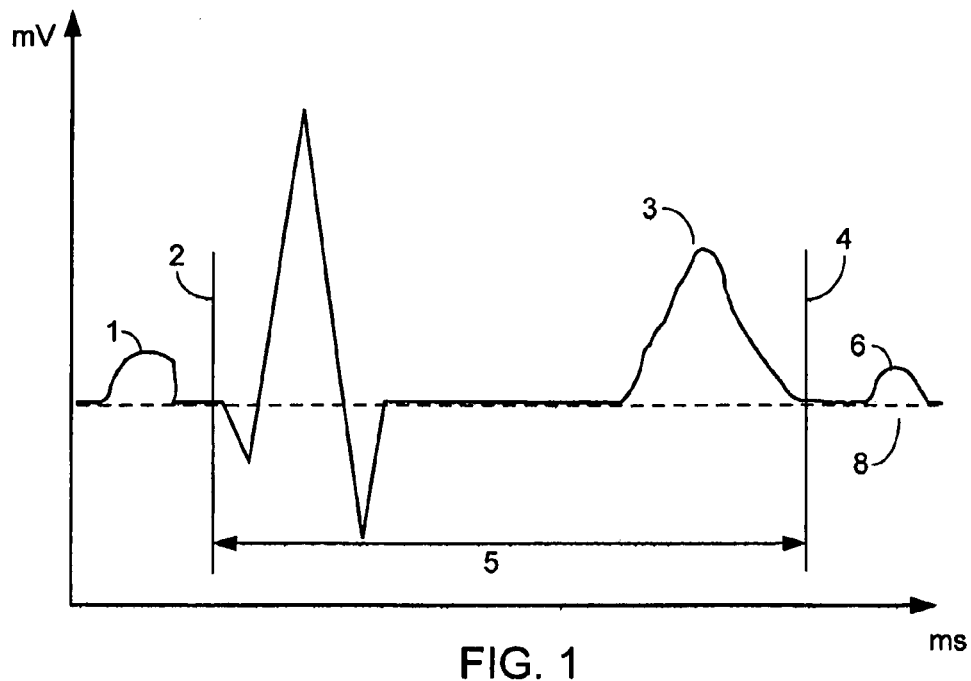
FIG. 1 represents the trace of a typical ECG signal.

FIG. 1 represents schematically the trace of a typical ECG signal, showing a single lead vector ECG signal. 1 is the P wave, 2 is the onset deflection of the Q wave (the start of the QT interval), 3 is the peak of the T wave, 4 is the approximate end of the QT interval, 5 is the QT interval duration to be measured, and 6 is the U wave. 8 is the isoelectric baseline of the ECG signal.

The X-axis represents time in milliseconds and the Y-axis represents millivolts above and below the isoelectric line baseline. The isoelectric line baseline is the voltage at which there is silent electrical activity within the myocardium, this being theoretically zero millivolts in the absence of noise.

The start of the QT interval is easily timed at 2 when the wave has high frequency content with a negative or positive deflection from a zero baseline value. The end of the QT interval is in theory the time at which the T wave returns to the isoelectric baseline. The isoelectric baseline is a theoretical line of constant voltage which in the absence of any noise is theoretically zero millivolts. To measure the QT interval 5, it is only necessary to subtract the one from the other.

As explained in the introduction, however, identifying the end of the T wave in real signals is difficult and somewhat subjective using known techniques.

FIGS. 2 to 6 will now be described which illustrate the novel steps proposed herein to derive the QT interval in a reliable manner. After describing these steps, a practical ECG apparatus incorporating automatic QT measurement using these techniques will be described, with reference to FIG. 7.

Minimisation of Noise

In addition to median ensembling and median smoothing either a wavelet thresholding method can be applied which will remove the frequency components identified in the isoelectric baseline (noise) from the rest of the ECG signal (explained below).

Figure 2:
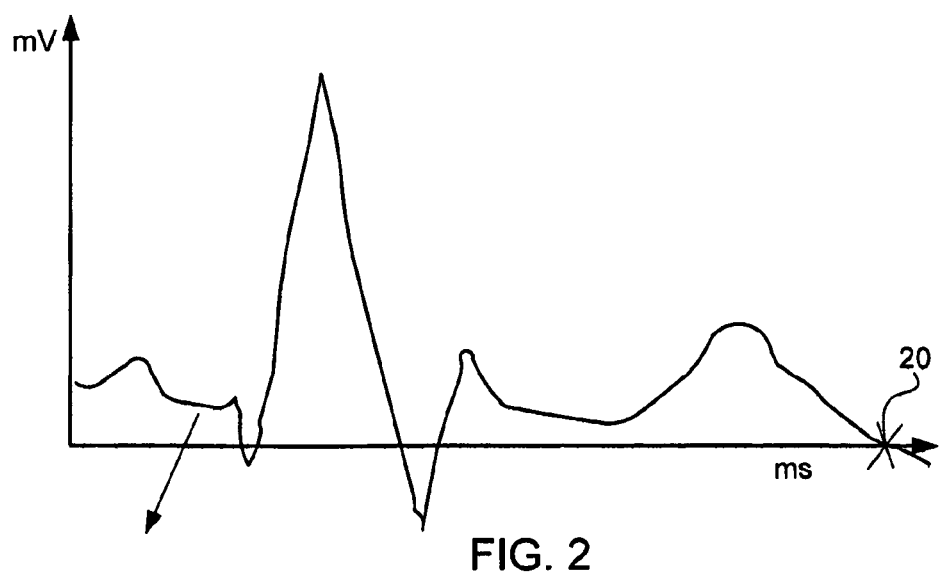
FIG. 2 shows an ECG signal where low frequency noise generates a drifting baseline.

FIG. 2 shows an ECG signal with low frequency noise generating a drifting baseline. The point 20 indicates the time point at which the signal has a zero millivolt value. The arrow shows the direction of rotation to required re-align the signal as described below.

Figure 3:
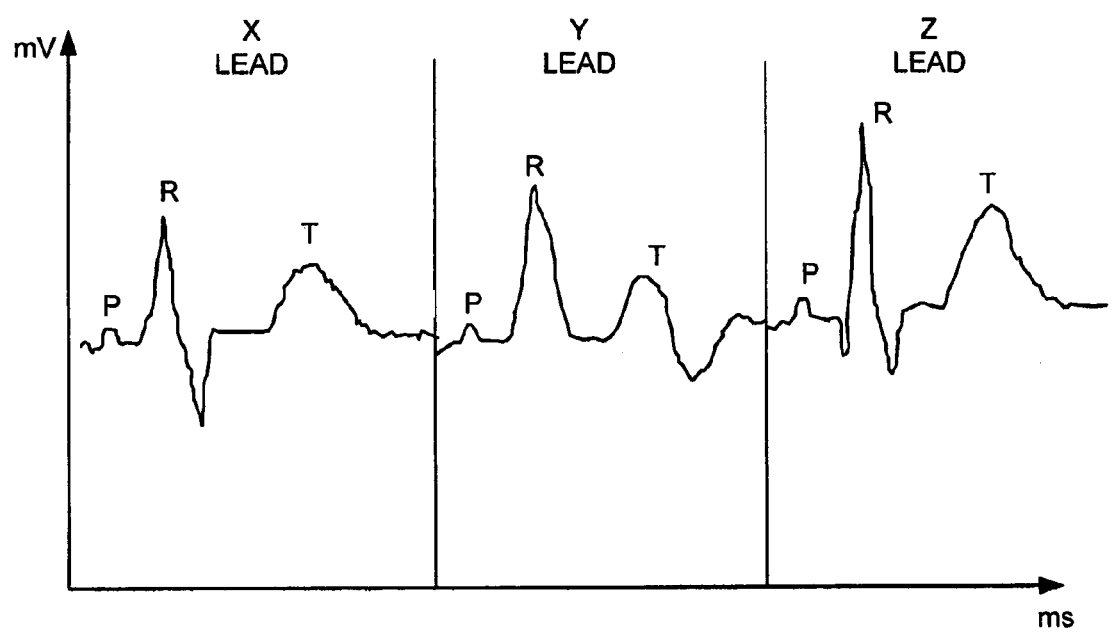
FIG. 3 shows the ECG signal of FIG. 2 simultaneously displayed in the XYZ orthogonal vectors.
Figure 4:
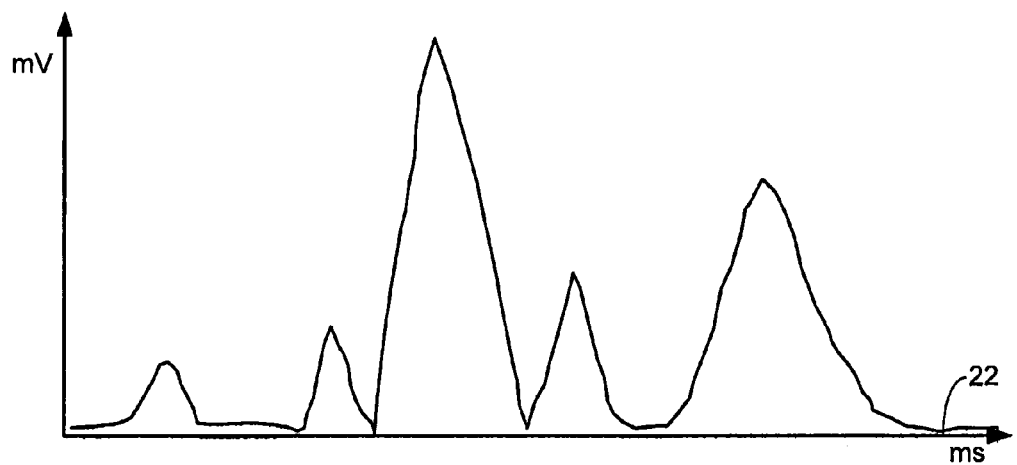
FIG. 4 shows summed squared voltages in the X, Y and Z orthogonal leads over the time period of the signal which gives the squared resultant vector of the ECG signal in three dimensions.

FIGS. 3 and 4 refer to a particular case of orthogonal XYZ leads but the noise minimisation method set forth below can be applied to any set of ECG leads suitable for recording an ECG signal, for example, the standard twelve lead system.

FIG. 3 shows the ECG signal of FIG. 2 simultaneously displayed in the XYZ orthogonal vectors. P is the P wave, R is the peak R wave, T is the peak T wave.

FIG. 4 shows summed squared voltages in the X, Y and Z orthogonal leads over the time period of the signal which gives the squared resultant vector of the ECG signal in three dimensions. P is the P wave; R is the peak R wave and T the peak T wave. The trough 22 is marked as that part of the downslope of the T wave which merges with the isoelectric line, that is, the time segment encompassing the end of the T wave, and prior to onset of the U wave.

Referring to FIGS. 2 to 4, in the method described herein, the low frequency baseline noise is firstly reduced by determining the median of the millivoltage values for multiple ensembled ECG signals from the given required vector leads. The median millivoltage signal for each time from, for example, ten ensembled ECG signals for each lead can be calculated to reduce low frequency baseline noise.

Next, the resulting median of the ensembled ECG signal is further smoothed by a moving median filter which has the advantage of reducing the high frequency noise without causing phase distortion.

Next a multiresolution Wavelet is used to obtain the magnitudes of noise frequency components which contaminates isoelectric baseline (which has zero frequency in the denoised state). In the wavelet method, for each frequency band, the maximum coefficient amplitude seen at the time of the isoelectric baseline within each frequency band is subtracted from the rest of the coefficients within that frequency band. The ECG waveform is then reconstituted from the addition of the detail coefficients for each frequency band.

The resulting median ECG signal is then shifted vertically so that the minimum values/value of the segment of the ECG following the peak T wave are/is zero millivolts. If it is observed that there is only a single time at which the signal value is zero, we judge that there is likely to be baseline drift. To correct this drift, the ECG is "rotated" in both clockwise and anticlockwise directions about the "zero value" axis until the ECG signal within trough 22 intersects the zero baseline at a second or multiple time points. The smallest angle of rotation necessary (which may be clockwise or anti-clockwise) will be accepted as that rotation necessary to correct for baseline drift, and this rotational correction is applied to the median ECG signal to derive the reconfigured ECG for each lead. Strict rotation is not necessary. Another geometric transformation such as a shear transformation may be equally appropriate to achieve the desired result.

The amplitude of the resulting median reconfigured ECG signal is then converted into microvolts and squared, which will have the effect of forcing the microvolt values below 1 towards zero whilst increasing the microvolt values above 1, thus effectively enhancing the high frequency features of the actual T wave signal end and reducing the low frequency features of the actual T wave signal end, thus making identification of the T wave end easier. The selection of a microvolt scale for this purpose is merely a matter of convenience, and a different scale factor could in principle be applied to keep the squared values within any desired range.

The above processing to minimise noise results in a squared reconfigured ECG signal of the type shown in FIG. 4 prepared for the QT interval measurement. Baseline drift has also been corrected.

QT Measurement Method

The method of measuring the QT interval can be applied to a reconfigured ECG signal in any vector lead. The onset of the Q wave can be identified readily in a known manner.

The method should be applied to a squared signal because it allows a clearer demarcation between isoelectric baseline and downslope of T wave. It also prepares the measurement for the squared Resultant vector and it keeps the T wave all positive. The method could theoretically be applied to cases of biphasic T waves which occur in certain pathological conditions.

Figure 5:
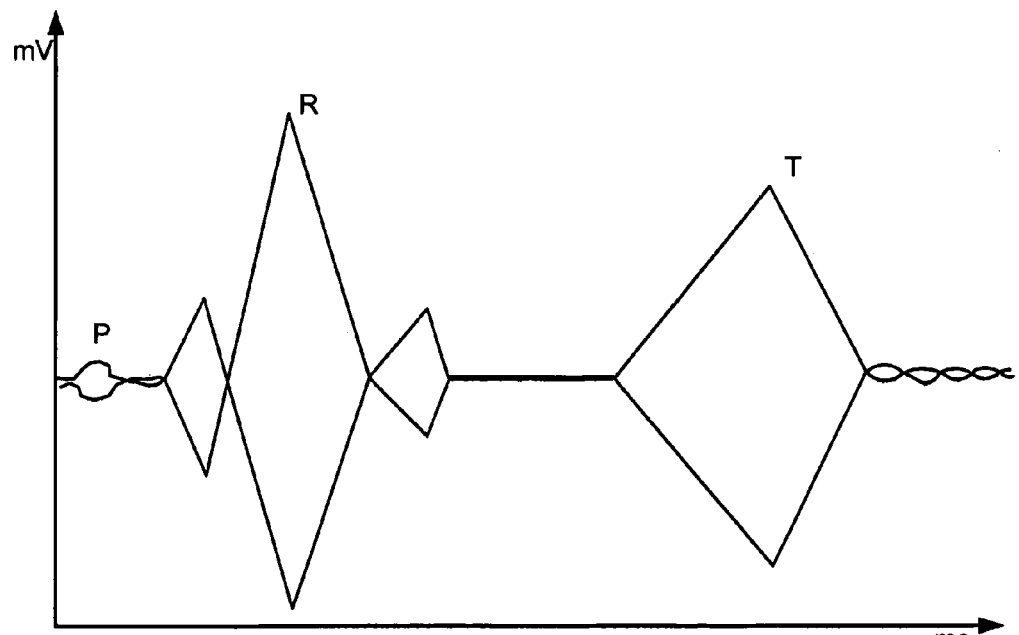
FIG. 5 shows an upright squared ECG signal and a superimposed inverted squared ECG signal.

FIG. 5 shows an upright squared ECG signal and a superimposed inverted squared ECG signal. They are superimposed with a vertical offset chosen so that the troughs of the isoelectric baseline following the peak T of both the upright and inverted waves have the best least squares fit.

Figure 6:
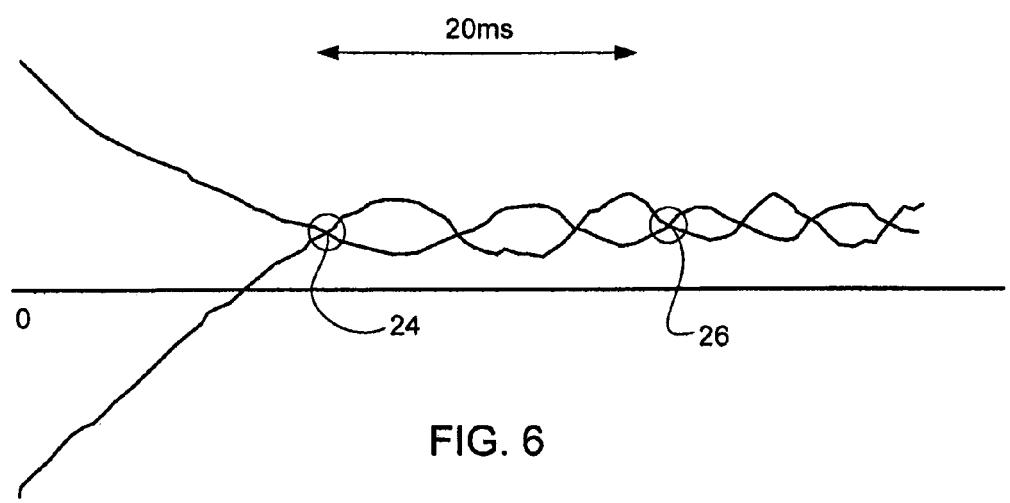
FIG. 6 is a magnified view of the superimposed part of the T wave downslopes and troughs about the isoelectric baselines from the upright and inverted ECGs of FIG. 5.

FIG. 6 shows a magnified view of the superimposed part of the T wave downslopes and troughs from the upright and inverted ECGs of FIG. 5, such that there is a least squares best fit between the waves. The two circles 24, 26 indicate the two times, separated by 20 milliseconds or more at which the millivolt values of the upright and inverted waves are identical.

Thus, the method to identify the end of the T wave comprises inversion of the reconfigured ECG without horizontal shifting and then merging of the inverted T wave with the reconfigured ECG signal. Referring back to FIG. 5, the exact timing of the T wave end can be defined as the first time of intersection at which the inverted version of the T wave intersects with the upright T wave of the reconfigured ECG signal, along the isoelectric line within the trough after the T wave peak shifted on the vertical axis to give the best least squares fit. This is the end of the T wave because it is the time at which both the upright T wave and the inverted version of itself return to the isoelectric line.

Referring now to FIG. 6, it can be shown that the true isoelectric line is the mean or median value calculated from the superimposed values of the upright and inverted waves, within the trough 22 following the peak T wave, which provide the best least squares fit. The end of the T wave can therefore be considered to occur in the trough at the first time point that there is no difference in millivoltage signal along this theoretical isoelectric line. For robustness, the method in this embodiment, checks for another point at which the two signals are identical, at a certain time further the tract. The time difference between the two time points (along the theoretical isoelectric line) at which the signal amplitudes are compared is arbitrary and a time of 20 ms has been adopted, though this time difference could be varied according to the noise content in the segment of the ECG deemed to be the isoelectric line. The time point can be variable, at least 20 ms, but up to any time along the isoelectric baseline before the next succeeding P wave or U wave if present.

QT Measurement of Resultant Vector

In an embodiment of the method, the QT interval of an electrocardiogram in any given lead can be measured. By measuring the QT interval of the squared vector resultant derived from quasi-orthogonal or actual orthogonal XYZ leads, the longest QT measurement in 3 dimensions can be made.

This avoids any apparent change in the QT interval of a fixed direction vector which may be caused by a dynamic physiological change in direction of the resultant vector in three dimensions, but without causing any change in length of the resultant vector QT interval.

QT Measurement Apparatus

Figure 7:
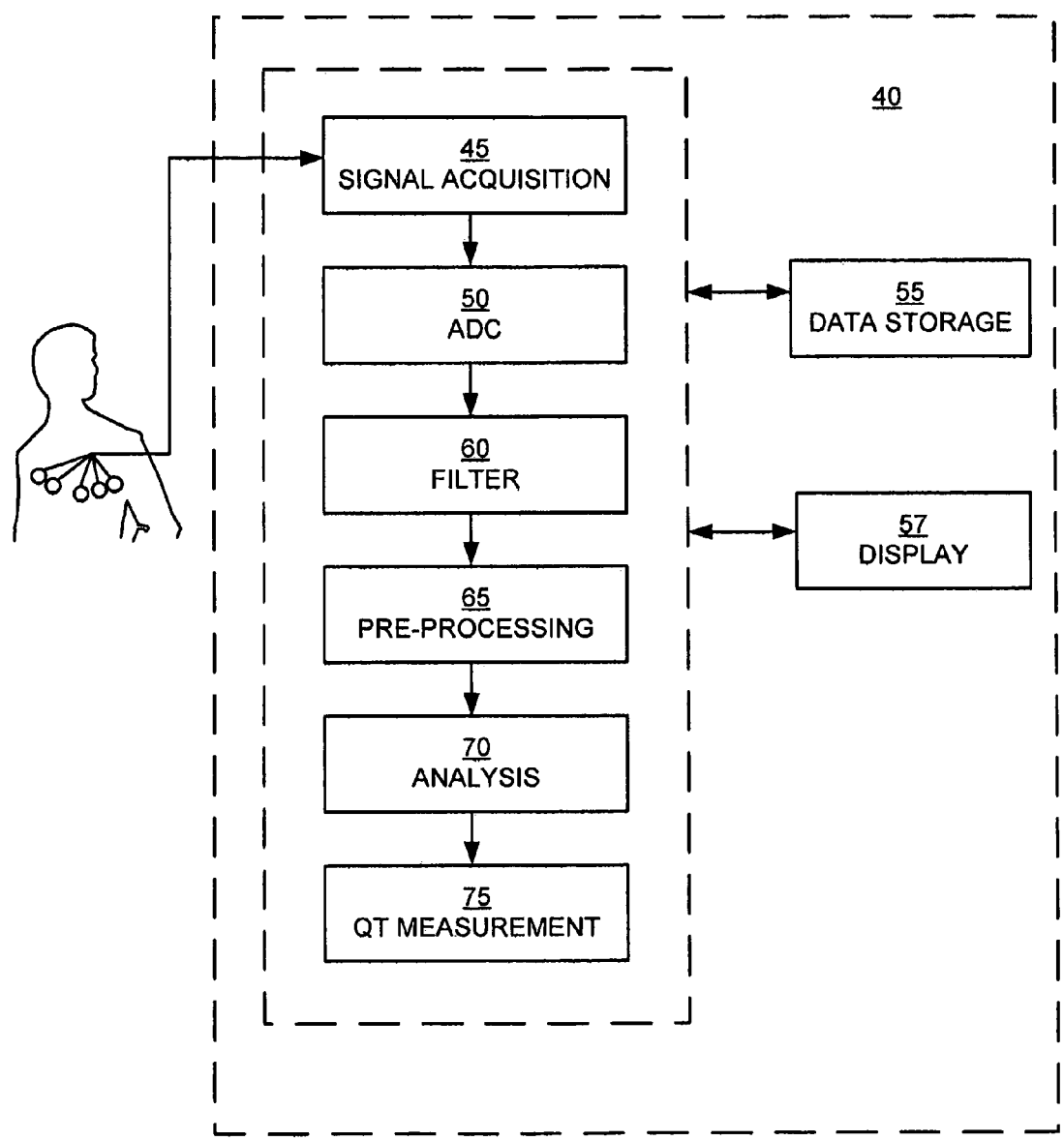
FIG. 7 is a diagram of an apparatus suitable for measuring automatically the QT interval of an ECG, in accordance with an embodiment of the present invention.

FIG. 7 is a diagram of an apparatus suitable for measuring the QT interval of an ECG by the method described above.

A subject 30 has a set of ECG leads 35 (or at least one lead) attached for the purpose of recording an ECG signal. The ECG signals are passed to an electronic system 40 for processing and analysing. The system 40 comprises a conventional signal acquisition module 45 which is connected by the lead wires to electrodes on the subject's body. The system further comprises an analogue to digital converter 50 connected to data storage 55 and filter 60. The filter is connected to a pre-processing module 65 which is connected to an analysis module 70 which is connected to a module for QT measurement 75.

The ECG leads and electrodes can be standard ECG electrodes and ECG monitoring sites, for example the standard 12 lead ECG sites, orthogonal or quasi-orthogonal ECG leads. The analogue to digital converter digitises the signal so that it may be processed to measure the QT interval. The filter 60 smoothes the ECG signal to remove noise, as discussed above. The pre-processing module performs the stages of duplicating and inverting the ECG signal, as discussed earlier. The analysis module carries out the steps of ascertaining the location of the different ECG features and QT measurement module performs the calculation of the QT interval as set forth above.

The system 40 is connected to data storage means 55 which can store the data acquired from the signal. The stored data can be the raw digitised ECG data, or as final processed data, or in some intermediary format. The storage can be hardware suitably integrated with the system 40, such as RAM, a hard drive, floppy drive, or such carrier medium, or be extended across a suitable connected communications network.

Similarly, the display 57 can be integrated with the system or connected separately, as a stand alone monitor for viewing data, a computer system's monitor, or suitable display connected across a communications network.

Analysis means 70 may further comprise means for further manipulating the ECG data. A method of determining the QT interval of an ECG wherein the Median millivoltage signal for each time from 10 ensembled ECG signals for each lead to reduce low frequency baseline noise is calculated. As previously described a Wavelet multiresolution analysis can be used to remove the noisy frequency content, present within the isoelectric baseline, from the whole ECG.

The complete system can be packaged as a standalone ECG monitoring and processing system or as apart of a larger system, for example, a suitable equipped computer. The modules 45 to 75 may be implemented in hardware, software, or a combination of both.

The invention claimed is:

1. A method of measuring a QT interval of an electrocardiogram (ECG) signal wherein an end of a T wave is identified from ECG data, the method comprising the steps of:
   (a) acquiring ECG signal data from a signal acquisition apparatus or from a data storage;
   (b) deriving a first set of ECG signal data from the acquired ECG signal data using an electronic system;
   (c) inverting the first set of ECG signal data to derive a second set of ECG signal data using the electronic system, said second set of ECG signal data comprising an inverted set of said first set of ECG signal data; and
   (d) determining the end of the T wave using the electronic system by reference to timing of at least one intersection at which an upright T wave of said first set of derived ECG signal data intersects an inverted T wave of a said second set of derived ECG signal data, the two sets of ECG data being superimposed so as to maximize data fit over a segment of ECG signal after a peak of the positive T wave.

2. The method as claimed in claim 1 wherein the data fit is maximised by a least squares calculation.

3. The method as claimed in claim 1, wherein:
   the steps of deriving a first set of ECG signal data from the acquired ECG signal data comprise deriving a first set of reduced noise ECG signal data from the acquired ECG signal data;
   the inverting step comprises inverting the first set of reduced noise ECG signal data to derive an inverted set of reduced noise ECG signal data; and
   the method further comprises the steps of:
   (e) identifying a portion of each set of ECG signal data corresponding to said segment;
   (f) calculating an offset such as to fit the first set of data to the inverted set of data over said segment;
   (g) detecting at least one intersection between the first set of data and the inverted set of data by reference to said offset; and
   (h) determining an end of said QT interval by reference to timing of the detected intersection.

4. The method as claimed in claim 3 wherein in step (h) the end of the QT interval is determined by a first point intersection.

5. The method as claimed in claim 4 wherein the end of the T wave is defined at the first point of intersection in said segment, provided there is at least one other point of intersection after a predetermined interval.

6. The method as claimed in claim 5, further comprising the steps of:
   determining the noise content in a segment of the ECG signal deemed to be an isoelectric baseline segment; and
   varying said interval according to noise content in said segment.

7. The method as claimed in claim 3 wherein:
   the signal acquisition apparatus comprises multiple ECG signal acquisition leads;
   the ECG signal data comprise an ensemble of ECG signals which have been acquired from the ensemble of multiple acquisition leads; and
   step (b) comprises calculating a median signal for each time from the ensemble of ECG signals for each lead to reduce low frequency baseline noise.

8. The method as claimed in claim 7 wherein the step (b) further comprises smoothing the median signal with a moving median filter to reduce high frequency noise.

9. The method as claimed in claim 8 wherein the step (b) further comprises filtering the smoothed median signal using a wavelet frequency thresholding technique which subtracts magnitudes of any non-zero frequency components within a segment of the ECG deemed to be an isoelectric baseline segment from the rest of the ECG signal thus further denoising it.

10. The method as claimed in claim 9 wherein the step (b) further includes vertically shifting the smoothed median signal so that a minimum value after peak of T is zero.

11. The method as claimed in claim 10 wherein the step (b) further comprises detecting and correcting baseline drift in the first set of ECG data.

12. The method as claimed in claim 11 wherein the detecting includes testing for presence of a single crossing of an isoelectric line by said first set of ECG data.

13. The method as claimed in claim 12 wherein the ensemble of ECG signals is rotated about a zero point to reconfigure the set of ECG data to have multiple crossings of said line.

14. The method as claimed in claim 7 wherein the step (b) further includes applying a non-linear function to the signal for all time instants, in order to accentuate features of interest and ensure positive deflections of the T wave.

15. The method as claimed in claim 14 wherein the step (b) further includes summing squared amplitudes of an ensemble of orthogonal leads over all time instants to give a squared resultant vector of the ensemble of ECG signals.

16. The method as claimed in claim 7 wherein the method further includes finding a beginning of the QT interval from the median of said ensemble of ECG signals from all of said leads.

17. The method as claimed in claim 16 wherein the method includes calculating the QT interval by subtracting the beginning of the QT interval obtained from the median of said ensemble of ECG signals from all of said leads from the end of the T wave determined in step (d).

18. The method as claimed in claim 1 wherein the QT interval is measured for squared vector resultant data derived from quasi-orthogonal or actual orthogonal XYZ leads, and a longest of QT measurements made in 3 dimensions is made.

19. The method as claimed in claim 3 wherein the ECG signal data is acquired in step (a) from a set of standard ECG leads including I, aVf and V2.

20. An apparatus for measuring the QT interval of an electrocardiogram (ECG) signal by identifying an end of a T wave from ECG data, said apparatus comprising:
   (a) means for acquiring ECG signal data;

(b) means for deriving a first set of ECG signal data from the acquired ECG signal data;

(c) means for inverting the first set of ECG signal data to derive a second set of ECG signal data, said second set of ECG signal data comprising an inverted set of said first set of ECG signal data; and (d) means for determining the end of the T wave, said T-wave being defined as a first time of intersection at which an upright T wave of said first set of derived ECG signal data intersects an inverted T wave of said second set of derived ECG signal data, the two sets of data being superimposed so as to maximise data fit over a segment of the ECG signal after a peak of the positive T wave.

21. The apparatus as claimed in claim 20 wherein the data fit is maximised by a least squares calculation.

22. The apparatus as claimed in claim 20 wherein the apparatus further comprises:

means for deriving a first set of reduced noise ECG signal data from the acquired ECG signal data;

means for inverting the first set of reduced noise ECG signal data to derive an inverted set of reduced noise ECG signal data;

means for identifying a portion of each set of ECG signal data corresponding to the segment;

means for calculating an offset such as to fit the first set of data to the inverted set of data over said segment;

means for detecting at least one intersection between the first set and the inverted set of data by reference to said offset; and means for determining an end of said QT interval by reference to timing of the detected intersection.

23. The apparatus as claimed in claim 22 wherein the acquired ECG signal data has been obtained from an ensemble of orthogonal leads is operable such that the QT interval is determined by a first point of intersection.

24. The apparatus as claimed in claim 23 wherein the end of the T wave is defined at the first point of intersection in said segment, provided there is at least one other point of intersection after a predetermined interval.

25. The apparatus as claimed in claim 24 further operable to determine the noise content in a segment of the ECG signal deemed to be an isoelectric baseline segment, and to vary said interval according to noise content in said segment.

26. The apparatus as claimed in claim 22 wherein, where the acquired ECG signal data has been obtained from an ensemble of ECG signals from multiple leads, the means for deriving a first set of reduced noise ECG signal data comprises means for calculating a median signal for each time from the ensemble of ECG signals for each lead to reduce low frequency baseline noise.

27. The apparatus as claimed claim 26 wherein the means for deriving a first set of reduced noise ECG signal data further comprises means for smoothing the median signal with a moving median filter to reduce high frequency noise.

28. The apparatus as claimed in claim 27 wherein the means for deriving a first set of reduced noise ECG signal data further comprises means for filtering the smoothed median signal using a wavelet frequency thresholding technique which subtracts magnitudes of any non-zero frequency components within a segment of the smoothed ECG median signal deemed to be an isoelectric baseline segment from the rest of the smoothed ECG median signal thus further de-noising it.

29. The apparatus as claimed in claim 27 wherein the means for deriving a first set of reduced noise ECG signal data further includes means for vertically shifting the smoothed median signal so that a minimum value after peak of T is zero.

30. The apparatus as claimed in claim 29 wherein the means for deriving a first set of reduced noise ECG signal data further comprises means for detecting and correcting baseline drift in the first set of ECG data.

31. The apparatus as claimed in claim 30 wherein detection the means for detecting includes means for testing for presence of a single crossing of an isoelectric line by said first set of ECG data.

32. The apparatus as claimed in claim 31 further comprising means for rotating said ensemble of ECG signals about a zero point to reconfigure the set of ECG data to have multiple crossings of said line.

33. The apparatus as claimed in claim 26 wherein the means for deriving a first set of reduced noise ECG signal data further includes means for applying a non-linear function for all time instants, in order to accentuate features of interest and ensure positive deflections of the T wave.

34. The apparatus as claimed in claim 33 wherein the means for deriving a first set of reduced noise ECG signal data further includes means for summing squared amplitudes of an ensemble of orthogonal leads over all time instants to give a squared resultant vector of the ensemble of ECG signals.

35. The apparatus as claimed in claim 20 wherein the apparatus further includes means for finding a beginning of the QT interval from the median of said ensemble of ECG signals from all of said leads.

36. The apparatus as claimed in claim 35 wherein the apparatus includes means for calculating the QT interval by subtracting the beginning of the QT interval, obtained from the median of said ensemble of ECG signals from all of said leads, from the end of the T wave obtained from said means for determining the end of the T wave.

37. The apparatus as claimed in claim 20 wherein the QT interval is measured for squared vector resultant data derived from quasi-orthogonal or actual orthogonal XYZ leads, and a longest of QT measurements made in 3 dimensions is made.

38. The apparatus as claimed in claim 20 wherein the ECG signal data is acquired from a set of standard ECG leads including I, aVf and V2.

39. A record carrier comprising recorded program instructions for causing a programmable processor to perform the steps of the method as claimed in claim 1.

* * * * *